(12) United States Patent
Healey (10) Patent No.: US 7,751,876 B2
(45) Date of Patent: Jul. 6, 2010

(54) METHOD AND SYSTEM FOR DETECTING PREMATURE VENTRICULAR CONTRACTION FROM A SURFACE ELECTROCARDIOGRAM

(75) Inventor: Jennifer Healey, Waltham, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 10 days.

(21) Appl. No.: 11/234,561

(22) Filed: Sep. 23, 2005

(65) Prior Publication Data

US 2007/0073176 A1 Mar. 29, 2007

(51) Int. Cl.
*A61B 5/0472* (2006.01)
(52) U.S. Cl. ..................................... 600/517
(58) Field of Classification Search ......... 600/516–518, 600/373, 374, 508, 509, 519, 521; 607/4, 607/5, 9, 25, 28, 119, 122
See application file for complete search history.

(56) References Cited

U.S. PATENT DOCUMENTS

| | | | | |
|---|---|---|---|---|
| 3,939,824 | A * | 2/1976 | Arneson et al. | 600/485 |
| 4,181,135 | A * | 1/1980 | Andresen et al. | 600/516 |
| 4,326,538 | A * | 4/1982 | Weigert et al. | 600/515 |
| 4,457,315 | A * | 7/1984 | Bennish | 600/517 |
| 6,609,028 | B2 | 8/2003 | Struble | |
| 6,728,572 | B2 | 4/2004 | Hsu et al. | |
| 6,745,074 | B1 * | 6/2004 | Obel | 607/9 |
| 6,871,089 | B2 | 3/2005 | Korzinov et al. | |
| 2004/0230105 | A1 | 11/2004 | Geva et al. | |
| 2005/0065443 | A1 | 3/2005 | Ternes | |

OTHER PUBLICATIONS

Zong, W. et al., "A Robust Open-source Algorithm to Detect Onset and Duration of QRS Complexes," *Computers in Cardiology 2003*, 30:737-740.
Senhadji, L. et al., "Comparing Wavelet Transforms for Recognizing Cardiac Patterns," *IEEE Engineering in Medicine and Biology*, Mar./Apr. 1995, p. 167-173.
Palreddy, S. et al., "A Multiple-Classifier Architecture for ECG beat classification," *Neural Networks for Signal Processing VII, Proceedings of the 1997 IEEE Workshop*, Sep. 24-26, 1997, pp. 172-181.
O'Leary, E.A. et al., "Detection of Low Level ST Segment Changes from the Ambulatory ECG and their Correlation with Ventricular Premature Beats," *Computers in Cardiology 2000*, 27:829-332, Sep. 24-27, 2000.
Casaleggio A. et al., "Neural Network for automatic anomalous QRS Complex Detection," *Computers in Cardiology 1990 Proceedings*, Sep. 23-26, 1990, pp. 553-556.
Nygards, M-E and Leif Sormo, "A QRS Delineation Algorithm with Low Sensitivity to Noice and Morphology Changes," *Computers in Cardiology*, 8:347-350, 1981.
Chang, W.H. et al., "Pattern Recognition Technique to QRS Complex Classification," *Proceedings of the 11th Annual International Conference of the IEEE Engineering in Medicine and Biology Society*, Nov. 9-12, 1989, vol. 1, pp. 32-33.

* cited by examiner

*Primary Examiner*—Carl H Layno
*Assistant Examiner*—Frances P Oropeza (57) ABSTRACT

A system and method for automatically detecting abnormal heart contractions originating in the ventricles, in a way that is independent of signal morphology is provided. As an uninterrupted series of ventricular detections indicates a possible ventricular arrhythmia, all ventricular beats are detected including isolated premature ventricular contractions (PVCs) and the associated R-R intervals are corrected. Premature ventricular contractions (ectopic beats) in non-standard lead configuration in a noisy signal from an ambulatory subject from a low-cost sensor that may be a small form factor sensor with 1 inch lead separation and may be rotated through multiple placements to correct an R-R interval time series used to detect atrial fibrillation.

11 Claims, 9 Drawing Sheets

METHOD AND SYSTEM FOR DETECTING PREMATURE VENTRICULAR CONTRACTION FROM A SURFACE ELECTROCARDIOGRAM

BACKGROUND OF THE INVENTION

Figure 1:
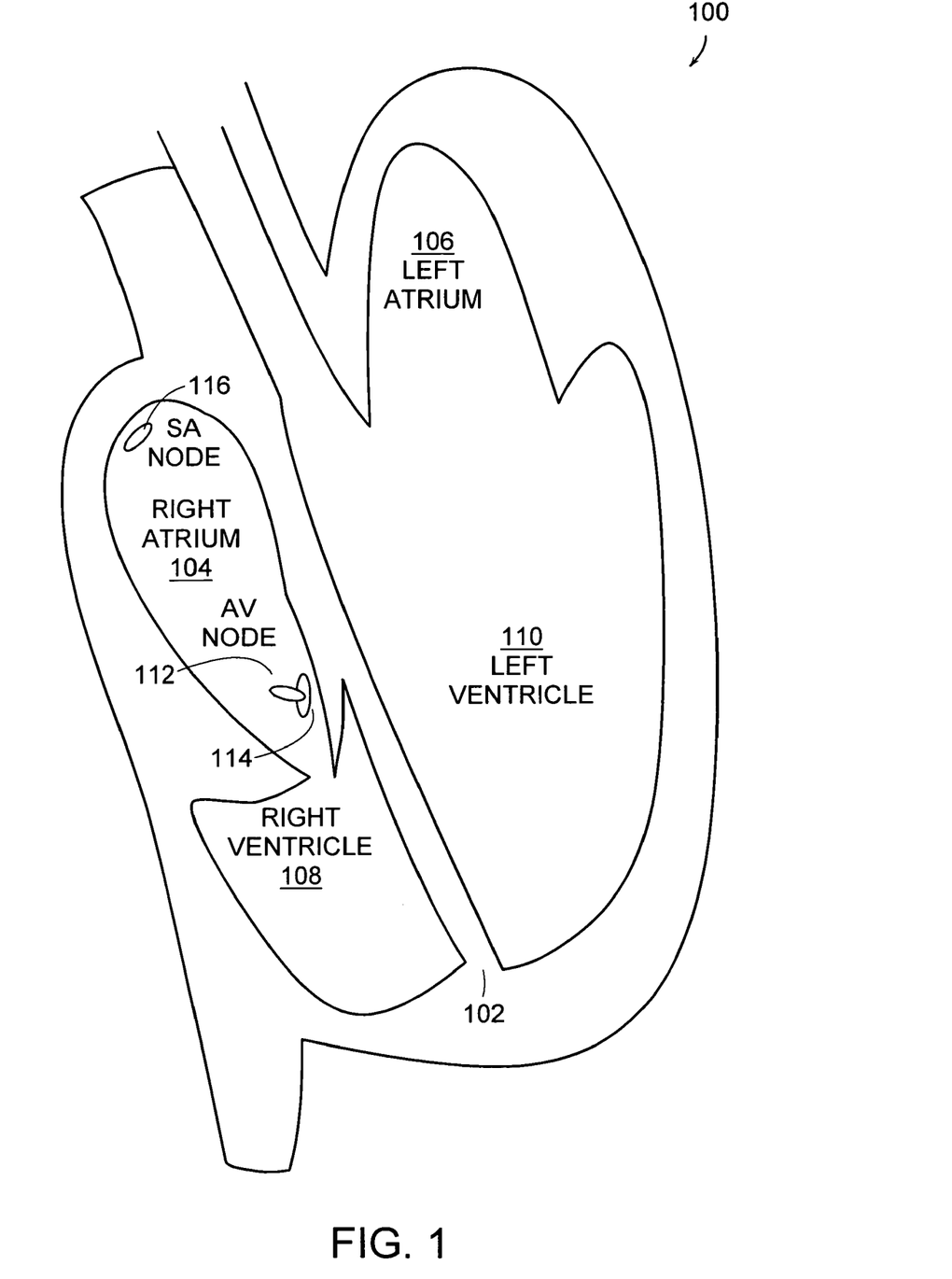
FIG. 1 is a diagram of the heart.

As shown in FIG. 1, the heart 100 is a pump, has four chambers and is divided into a right side and a left side by a muscular wall called the septum 102. The two chambers at the top are called the right atrium 104 and the left atrium 106 and the two chambers at the bottom are called the right ventricle 108 and the left ventricle 110. The atria and ventricles work together, contracting and relaxing to pump blood out of the heart.

Oxygen-poor blood enters the top of the heart through the inferior and superior vena cava veins and flows into the right atrium 104 and passes through the tricuspid valve to the right ventricle 108. After the right ventricle 104 fills, it contracts and blood flows through the pulmonary valve to the lungs. Oxygen-rich blood from the lungs enters the left atrium 106 through the pulmonary vein and through the left atrium 106 to the left ventricle 110. The left ventricle pumps the blood into the aorta.

The heart also has an electrical system that includes a pacemaker to control the contraction of the heart chambers. Normal heart rhythm is termed sinus rhythm. During normal sinus rhythm, the heartbeat starts with a miniature electrical impulse in the sinoatrial (SA) node 116, also referred to as the heart's "natural pacemaker" located in the right atrium 104. The electrical signal spreads across the atria and via the atrioventricular (AV) node 112 to the ventricles. The AV node 112 is a small mass of specialized cardiac muscle fibers that receives impulses from the SA node 116 and directs them to the walls of the ventricles. The AV node 112 creates a brief delay (about one tenth of a second) in the impulse to allow the atria to contract and force blood into the ventricles and then spreads the impulses rapidly across the ventricles to make them contract. The ventricles are electrically isolated from the atria and electrical signals reach them via the AV node 112.

The AV node 112 connects to a group of fibers (the His-Purkinje system) in the ventricles that conducts the electrical signal. A bundle of His 114 connected to the AV node 112 transmits the electrical impulses from the AV node 112 to the distal His-Purkinje system which extends throughout the endocardium of the right and left ventricles 108, 110. The electrical impulses reach the cells of the ventricles, causing cardiac muscles in the ventricles to contract. The ventricles are the muscular part of the heart that actually pump the blood.

An electrocardiogram (ECG or EKG) is a graphic tracing of the variations in electric potential caused by the excitation of the heart muscle plotted along a time axis. The variations in electric potential are detected at the body surface through electrodes that are placed on different parts of the body (limbs, chest wall). The signals are amplified and recorded by the electrocardiograph. The electrocardiograph is an instrument for recording the changes of electrical potential. The ECG records the depolarization (stimulation) and repolarization (recovery) potentials generated by the atrial and ventricular myocardium.

Figure 2:
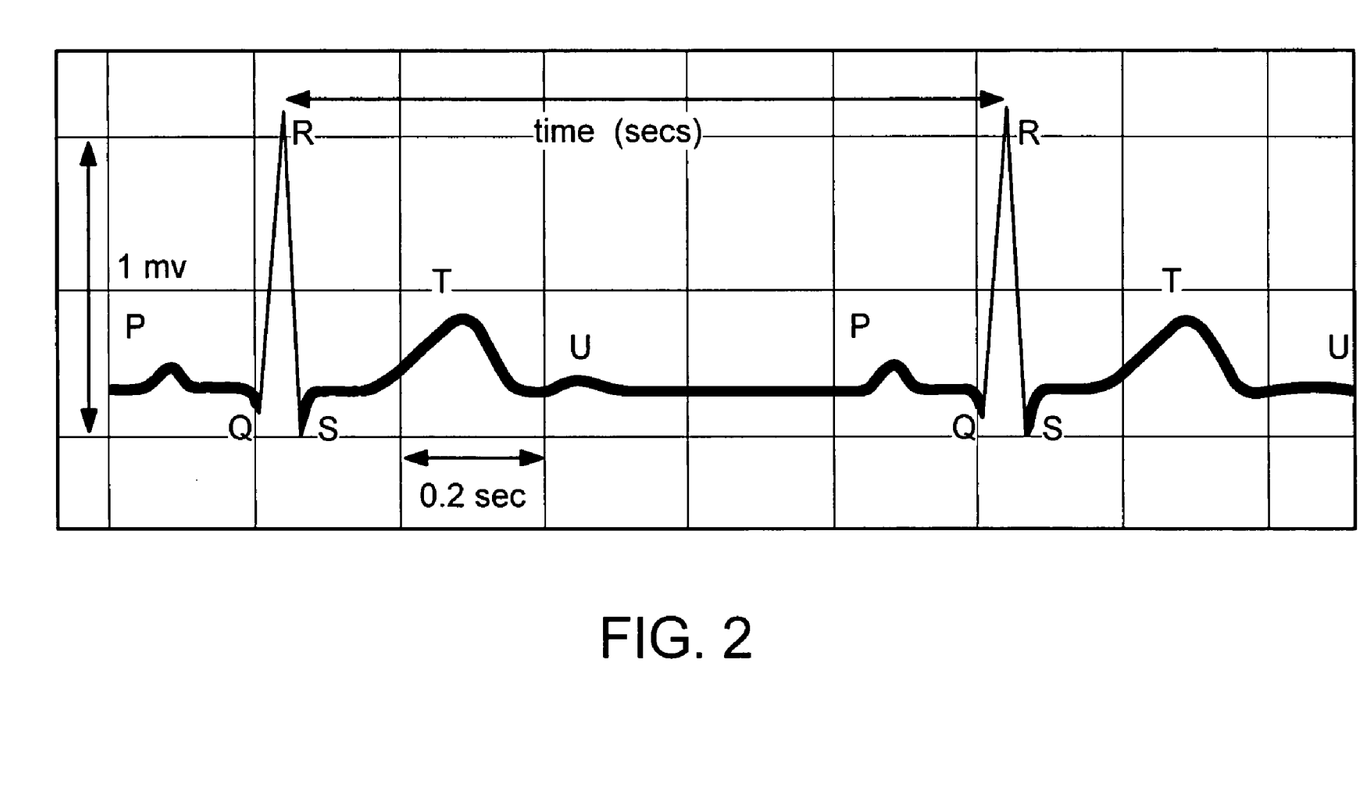
FIG. 2 is a schematic illustration of an output from an electrocardiogram for a normal heart rhythm.

FIG. 2 is a schematic illustration of an output from an electrocardiogram for a normal heart rhythm. The electrocardiogram shows the deflections resulting from atrial and ventricular activity. A typical electrocardiogram consists of a regular sequence of deflections (waves), labeled P, QRS, T and U. The first deflection (P) is due to excitation (contraction) of the atria. The QRS deflections are due to excitation (depolarization) of the ventricles. The T wave is due to recovery of the ventricles (repolarization). The U wave is a potential undulation of unknown origin immediately following the T wave. The amplitude of each of these components (deflections) is dependent on the orientation of the heart within the individual and the electrodes used to record the ECG.

The heart rate is the number of times the heart beats per minute which can be calculated by counting the average number of beats for a given duration (typically 15-30 seconds). The linear distance between neighboring peaks of simultaneous heart beats on an ECG corresponds to the time necessary for a single cardiac cycle (heart beat). As illustrated in FIG. 2, the linear distance (labeled "time") is measured between the peaks of neighboring QRS complexes.

The distance between the R waves in a given ECG signal is variable. When an ECG is performed, it is common to measure the heart rate for several cardiac cycles to determine how consistently the heart beats. In addition to analyzing whether the interval between waves from consecutive cardiac cycles remain consistent, the individual that analyzes the ECG also looks for how fast the heart is beating, the consistent shape of each wave, and the normality of duration and configuration of each wave.

An arrhythmia is an irregularity from the normal rhythm of the heart. Atrial fibrillation is an arrhythmia that is characterized by a rapid irregular heartbeat. Atrial fibrillation (AF) is a common sustained arrhythmia in which the atria contract rapidly and irregularly in a chaotic manner due to multiple electrical signals firing at 400 to 600 beats per minute. The AV node 112 (FIG. 1) filters out most of the additional electrical signals. However, more electrical signals reach the ventricles 108, 110 (FIG. 1) than normal, resulting in the ventricles beating at rates of 110 to 180 beats per minute faster than normal resting heart rate which is between 60 and 80 beats per minute.

AF is not immediately life threatening, but the risk of stroke is increased because the quivering atria beat too rapidly to contract effectively and with time they enlarge, which can lead to blood clots forming within the atria. If a blood clot leaves the heart and lodges in the brain, a stroke results. Also, the rapid beating of the ventricles for prolonged periods can result in weakening them which can lead to heart failure.

Often the symptoms of atrial fibrillation occur infrequently and can only be detected by continuous monitoring over a long time period on an ambulatory subject using a small portable ECG recorder, called a Holter monitor (continuous ambulatory electrocardiograph monitor). Electrodes are taped to the chest and wires are connected to a portable battery-operated recorder.

Standard practice for using an ambulatory monitor requires electrode placement in known positions on the body in order to perform either visual analysis or analysis by a computer program using template matches on the recorded signal because the QRS complex differs dependent on position of the electrode. The analysis of each trace is dependent on the position of the electrode corresponding to the trace. The analysis involves comparing the trace with a stored template of a normal trace at the same position. Thus, the placement of the electrodes is critical to the analysis and is performed by a person who has received special training in the placement of the electrodes. The need for a person skilled in placement of the electrodes increases the cost of the ECG and limits the use of the test to those who have already exhibited symptoms.

The ECG signal may include isolated premature ventricular contractions (PVCs) which are abnormal heart contractions that originate in the ventricles. An uninterrupted series of ventricular detections indicates a possible ventricular arrhythmia which may be fatal. However, isolated premature ventricular contractions may occur in patients with or without heart disease. A PVC event results from irritated ectopi foci in the ventricular area of the heart which cause premature contractions of the ventricles. The premature contractions are independent of atrial depolarization. As the QRS complex occurs earlier with a premature ventricular contraction and has a wider morphology, inaccuracies in measurement of R-R intervals of the beats before and after the premature ventricular contraction are common.

Typically, PVCs are identified using correlation with a template that matches known signal morphology and requires assumptions about the placement of the leads. The identified PVCs can then be removed from the ECG signal or beat detections can be corrected to prevent confounding R-R interval variance which is an indicator used in atrial fibrillation monitoring. Typically, the removal of the identified PVCs is performed manually by a technician performing the verification. Alternatively, the template matching can be performed by a computer.

SUMMARY OF THE INVENTION

The present invention addresses the problem of automatically detecting abnormal heart contractions originating in the ventricles, in a way that is independent of signal morphology. As an uninterrupted series of ventricular detections indicates a possible ventricular arrhythmia, all ventricular beats are detected including isolated premature ventricular contractions (PVCs) and the associated R-R intervals are corrected.

The method offers the advantage of being independent of any particular ECG morphology because it detects PVCs in a line integral transformed space. This allows the method to be used in non-standard electrode lead placements and allows seamless detection as the device is moved to multiple locations. This method can be used with wearable device that can be placed in a different location each day to reduce skin irritation.

The system detects premature ventricular contractions (ectopic beats): 1) in non-standard lead configuration 2) in a noisy signal from an ambulatory subject 3) from a low-cost sensor 4) from a small form factor sensor with 1 inch lead separation 5) from a sensor rotated through multiple placements. The detection of premature ventricular contractions can be used to correct an R-R interval time series used to detect atrial fibrillation.

In a preferred embodiment, a computer implemented method for automatically detecting premature ventricular contraction in an ECG signal transforms the ECG to a line integrated signal. The peak values of the line integrated signal near the points of QRS complexes detected in the ECG signal are compared with a threshold to provide an indication of whether the peak represents a premature ventricular contraction.

The average value of peaks in the line integrated signal may be computed. The threshold is between seventy and eighty percent of the average value of peaks. The width of a peak is compared with an average width of peak to provide an indication of whether the peak indicates a premature ventricular contraction. The peak having a width that is between thirty five and twenty five percent of the average width indicates a premature ventricular contraction.

The position of detected QRS complexes corresponding to detected premature ventricular contractions may be corrected based on peak values in the line integrated signal.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Most ECG recordings contain two or more simultaneously recorded ECG signals, called "leads." The heart generates an electrical field that varies spatially as well as temporally. Thus, the standard practice is to record two or more signals (leads) derived using sensing electrodes placed at certain specific locations. The wires that connect the electrodes to the recording equipment are also sometimes referred to as "leads".

As is well-known in the art, there is a standard placement for ECG leads that requires an individual with special training to perform the placement. Typically, a nurse performs the placement, a doctor performs the testing, an ECG technician runs the analysis software and a cardiologist performs the over-read. Non-ambulatory electrocardiograph devices include precordial leads and limb leads. Precordial leads are placed at pre-defined positions on the chest wall referred to as V1-V6. Position V1 is in the fourth intercostal space at the right sternal border, V2 is in the fourth intercostal space at the left sternal border, V3 is mid-way between V2 and V4, V4 is in the fifth intercostal space in the mid-clavicular line, V5 is in the left anterior axillary line at the level of V4 and V6 is in the left mid-axillary line at the level of V4. The limb leads are placed on the right and left wrists and the right and left ankles. Limb leads are not generally used in ambulatory electrocardiograph devices because physical activity causes significant interference in these leads.

A major problem with ECG is the difficulty of ensuring that electrodes are properly positioned. The present approach addresses the problem of detecting the heart condition known as Premature Ventricular Contractions (PVCs), that is, abnormal heart contractions originating in the ventricles. A premature ventricular contraction occurs when a beat starts in the ventricles instead of in the atria.

The PVCs are detected in a way that is independent of signal morphology and thus can be detected using an ambulatory electrocardiograph device that does not require placement of electrodes at specified positions on the body.

The present approach for detecting premature venticular contractions (PVCs) relies on features of the electrical signal that correspond directly to the physiological characteristics of contractions originating in the ventricles. One characteristic is that contractions originating in the ventricles propagate more slowly than contractions that originate in the atria. This is a result of the difference in the electrical pathways. Signals originating from the atria travel through the more conductive "bundle of His" 114 (FIG. 1) whereas contractions originating in the ventricles travel through the less conductive ventricular heart muscle. Due to the difference in conductions, a ventricular contraction is slower and the main part of the contraction appears wider on an electrocardiogram. An isolated premature ventricular contraction (VPC) is also referred to as an isolated ventricular premature complex (VPC). An isolated premature ventricular contraction (VPC) is also referred to as an isolated ventricular premature complex (VPC) or a ventricular ectopic beat (VEB). A VPC is recognized by a QRS interval (duration of the QRS complex) that is longer than during a sinus rhythm. The QRS complex is not preceded by P waves. In a normal sinus rhythm of 75 beats per minute, the QRS interval is approximately 0.08 s. There is some variance in the QRS interval both due to different sizes and conductive pathways in the hearts of different individuals and potentially depending on the electrode placement used to record the ECG. The QRS interval of a premature ventricular contraction (VPC) ranges from 0.12 s-0.16 s and multiple morphologies may be present.

In one embodiment, an ambulatory electrocardiograph device is designed for long term (greater than 24 hours) wearability and as such is small with electrodes much closer together than is typical in clinical applications. Sensors attachable to the chest wall can be moved daily to a randomly chosen position on the chest wall by the individual being tested to avoid skin irritation from the electrode adhesives. The electrocardiogram (ECG or EKG) signal generated by the ambulatory electrocardiograph device is non-standard, has changing morphology (form and structure) and contains significant muscle noise because the individual is ambulatory while being monitored.

The ambulatory electrocardiograph device can include memory for storing the ECG signal received through the electrode. The ambulatory electrocardiograph can periodically download the stored ECG signal to a computer system for analysis. In one embodiment, the stored ECG signal is downloaded to the computer system through a wireless communication interface to a wireless network. In an alternative embodiment, the stored ECG signal is transmitted to the computer system over a telephone network. In yet another embodiment, the ECG signal is stored in removable storage in the ambulatory device for later analysis by another computer system.

In one embodiment, the computer system that analyzes the ECG signal is separate from the ambulatory electrocardiograph device (sensor) in order to conserve power on the device, and to reduce the cost and weight of the device by using remote computations and storage of the recorded ECG signal. The ECG signal is analyzed at a remote site from the sensor by a technician or other qualified person and the individual receives notification of the verified results. In order to prevent the individual being monitored from receiving notification of false triggers, notification of detection of AF is hidden from the individual by analyzing the ECG signal at a remote site. In an alternate embodiment, the analysis can be performed in the sensor with the notification of AF being hidden from the individual being monitored, for example, the notification can be transmitted to a remote computer system without alerting the individual.

Figure 3:
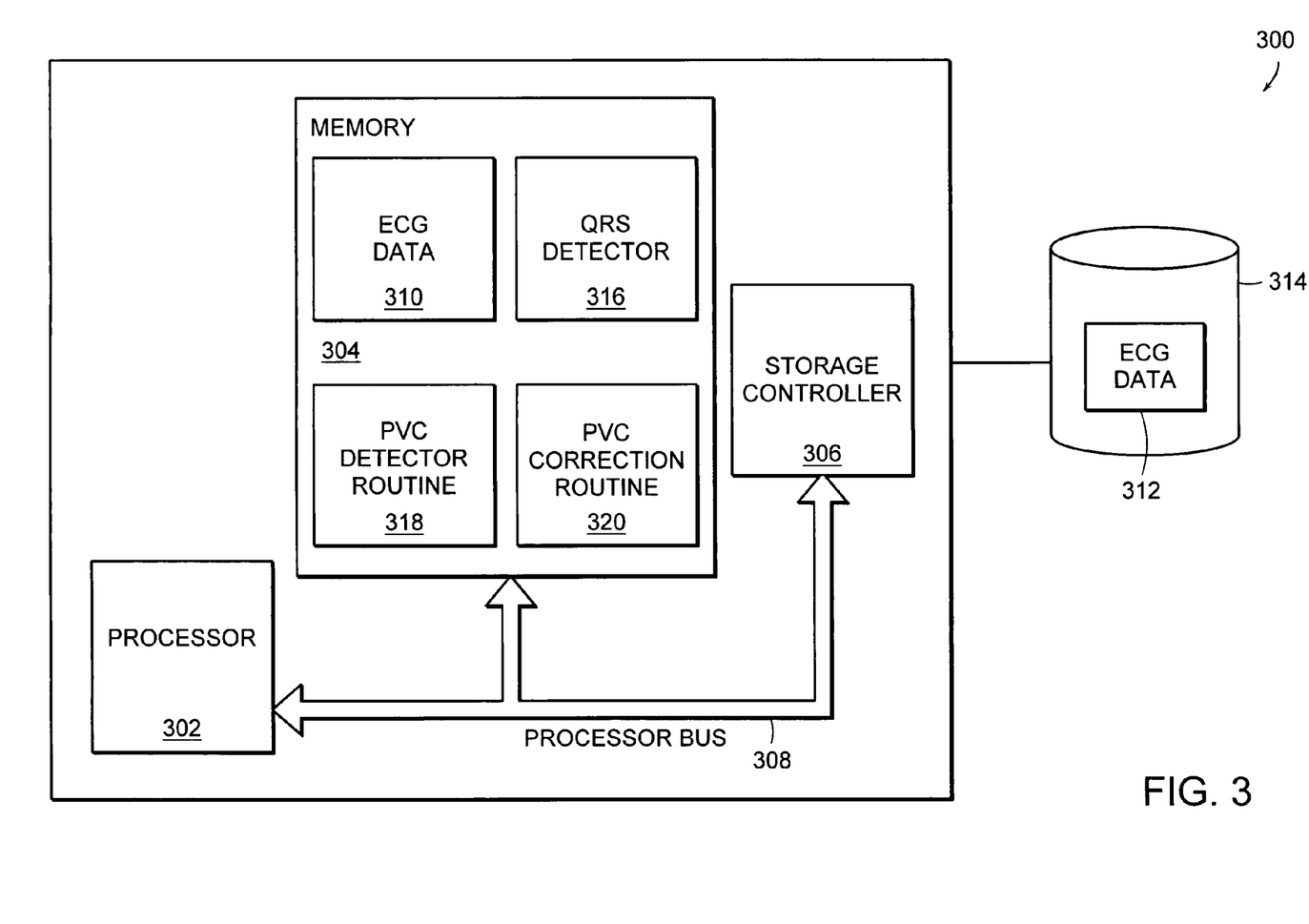
FIG. 3 is a block diagram of a computer system 300 in which the present invention is utilized.

FIG. 3 is a block diagram of a computer system 300 in which the present invention is utilized. The computer system 300 includes a processor 302, memory 304 and a storage controller 306 coupled to secondary memory such as, a disk drive 314. The processor 302 is coupled to the memory 304 and the storage controller 306 through a processor bus 308. The storage controller 306 controls the disk drive 314.

The ECG signals (ECG data) collected by ECG devices such as an ambulatory device can be stored in ECG data 310 in the memory 304 or in ECG data 312 on the disk drive 314. The memory 304 also stores routines executable by the processor 302 to automatically detect premature ventricular contractions (PVCs) in the ECG signal. The routines include a QRS detector 316 that computes R-R intervals in the ECG data. A PVC detector routine 318 detects PVCs in the R-R intervals computed by the QRS detector 316. A PVC correction routine 320 identifies the true QRS peak corresponding to the PVC.

Figure 4:
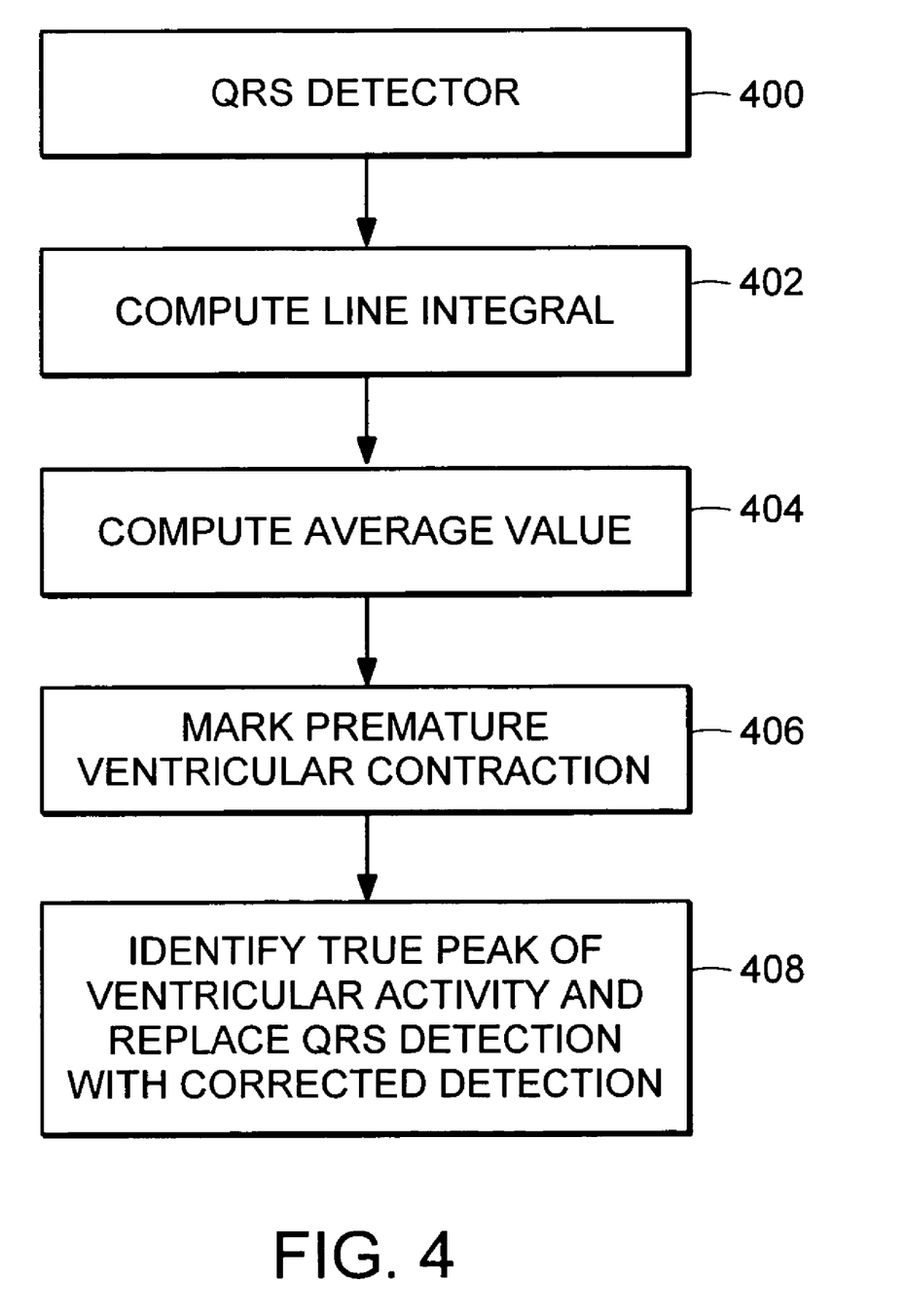
FIG. 4 is a flowchart illustrating a technique for detecting PVCs in the ECG signal according to the principles of the present invention.

FIG. 4 is a flowchart illustrating a technique for detecting PVCs in the ECG signal according to the principles of the present invention.

At step 400, a morphology-independent single-channel QRS detector routine 316 is used to determine R-R intervals in the ECG signal (lead) by detecting the QRS complex.

ECG leads record the difference in potential between electrodes placed on the surface of the body. Returning to FIG. 2, the ECG waves (deflections) are labeled alphabetically starting with the P wave. The P wave represents atrial depolarization. The QRS complex represents ventricular depolarization. The ST-T-U complex (ST segment, T wave, and U wave) represents ventricular repolarization. There are four major ECG intervals: R-R, PR, QRS and QT.

The QRS complex is subdivided into specific deflections or waves. If the initial QRS deflection in a given ECG lead is negative, it is termed a Q wave. The first positive deflection is termed an R wave. A negative deflection after an R wave is an S wave.

The heart rate can be computed from the R-R interval. AF is characterized by disorganized atrial activity, resulting in an ECG without discrete P waves. A secondary effect of this disorganized atrial activity is irratic ventricular contraction, resulting in an ECG with high R-R interval variation. The variance of R-R intervals in an ECG signal is a good indicator of atrial fibrillation. If there is an indication of atrial fibrillation further testing can be performed on the subject. Although this test is not as accurate as other available tests, it is inexpensive to perform and provides an indication as to whether more expensive testing is warranted.

The shape of the QRS complex in an electrocardiogram differs depending on where the sensing electrodes are placed on the body. The R-wave spike in the QRS complex can either be upwards pointing, downwards pointing or can have both up and down components. In standard 12-lead electrocardiography, six successively placed leads along the first floating rib from the midline of the subject body to the side will normally show an "R-wave progression" from an upwards to a downwards spike. A morphology independent QRS detector allows accurate calculation of R-R intervals regardless of the sensor's placement on the chest wall. One such morphology independent QRS detector is described in "A Robust Open-source Algorithm to Detect Onset and Duration of QRS Complexes", W. Zong, G. B. Moody, and D. Jiang, Computers in Cardiology 2003, 30:737-740, the contents of which are incorporated herein by reference in its entirety. This QRS detector routine is an open-source routine and is available at www.physionet.org/physiotools/wag/wqrs-1.htm. This technique implements a linear transform of the ECG signal. Using this transform, for each time window, w, the length of the line of the ECG signal over that time is calculated. The result is a line transform of the ECG where each point represents a successive line integral of a sliding window, w. The QRS spike is the most prominent feature in an ECG signal and the least affected by muscle noise allowing the R-R intervals to be computed.

In one embodiment, the QRS detector 316 uses the WQRS single-channel QRS detector described in W. Zong, G. B. Moody, D. Jiang, "A Robust Open-source Algorithm to Detect Onset and Duration of QRS Complexes" Computers in Cardiology 2003, 30:737-740 incorporated herein by reference in its entirety. The QRS detector 316 detects onset of QRS complexes and is insensitive to QRS morphology change. A non-linear scaling factor for ECG curve length enhances the QRS complex and suppresses other parts of the ECG signal and noise.

The QRS detector routine 316 detects onset and duration of QRS complexes. Using the QRS detector routine, the ECG signal (data) 310 stored in memory 304 in the AF detection system is input to a low-pass filter which produces a filtered ECG signal. The ECG data can be a low quality ECG signal that has been received from an ambulatory electrocardiogram device. For the adult human, the ideal passband for the low-pass filter is about 5-15 Hz. The filtered ECG is input to a curve length transformation which converts the filtered ECG signal to a curve length signal. The QRS detector 316 is stable and insensitive to QRS morphology change. The curve length transformation converts the filtered ECG signal to a curve length signal by introducing a nonlinear scaling factor to enhance the QRS complex and suppress unwanted noise. The present approach detects ventricular contractions in a way that is independent of any particular electrode placement configuration.

Figure 5:
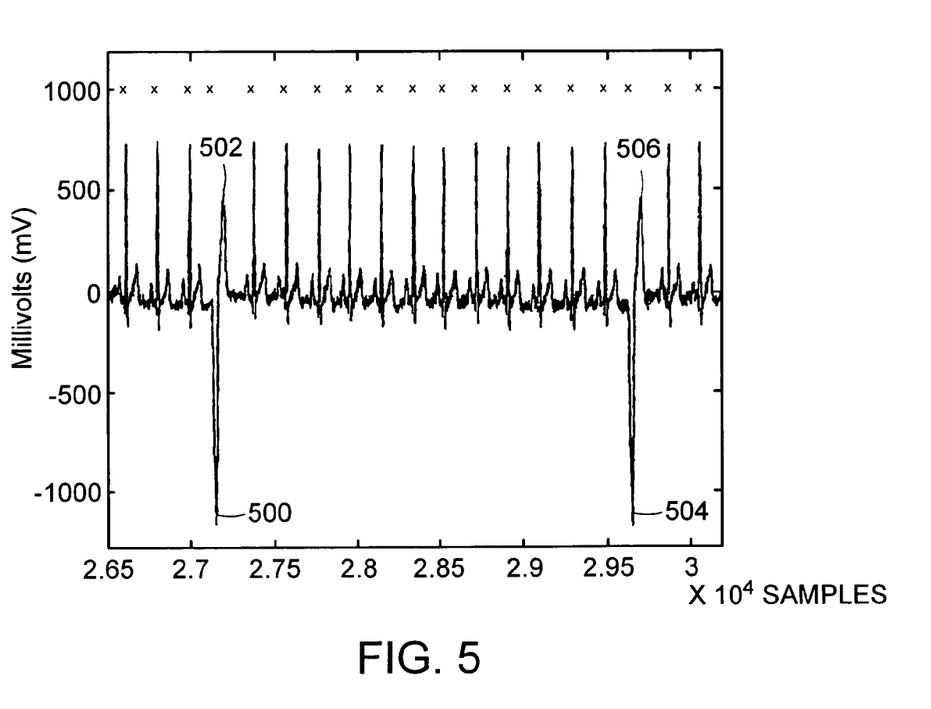
FIG. 5 is a simulator generated ECG signal showing two PVC's located at 27200 samples and 29700 samples.

FIG. 5 is a simulator generated ECG signal showing two PVC's located at 27200 samples and 29700 samples. Each PVC is characterized by a sharp downward spike 500, 504 followed by an upward spike 502, 506. The different morphology of the PVC causes the QRS detector to trigger on the sharp downward part of the signal rather than on the wider upward spike that represents the true ventricular activity. Above the ECG signal, x marks indicate the detection of QRS complexes.

With a different electrode placement, the PVC will have a different morphology, but the premature ventricular contraction is always represented by the slower, wider part of the electrical signal.

The present approach detects premature ventricular contractions in a way that is independent of any particular electrode placement configuration.

Returning to FIG. 4, at step 402, the original electrical signal is transformed by taking its line integral so that PVCs are detected in a manner that is independent of the electrode placement.

The line integrated value is computed by taking the sum of the absolute values of the differences of successive points over a window (w) using the equation below:

$$\sum_{i=0}^{W} |x_-i - x_-(i+1)|$$

Figure 6A:
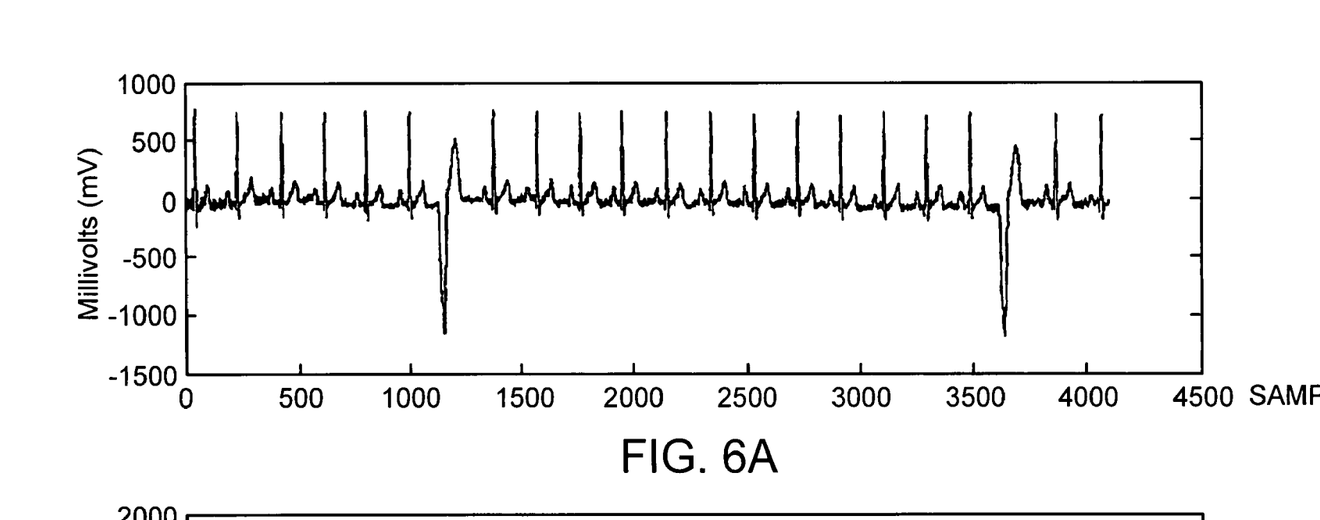
FIG. 6A illustrates an electrical signal with three ECG series with two PVCs, one PVC at 1200 samples and the other PVC at 3700 samples.
Figure 6B:
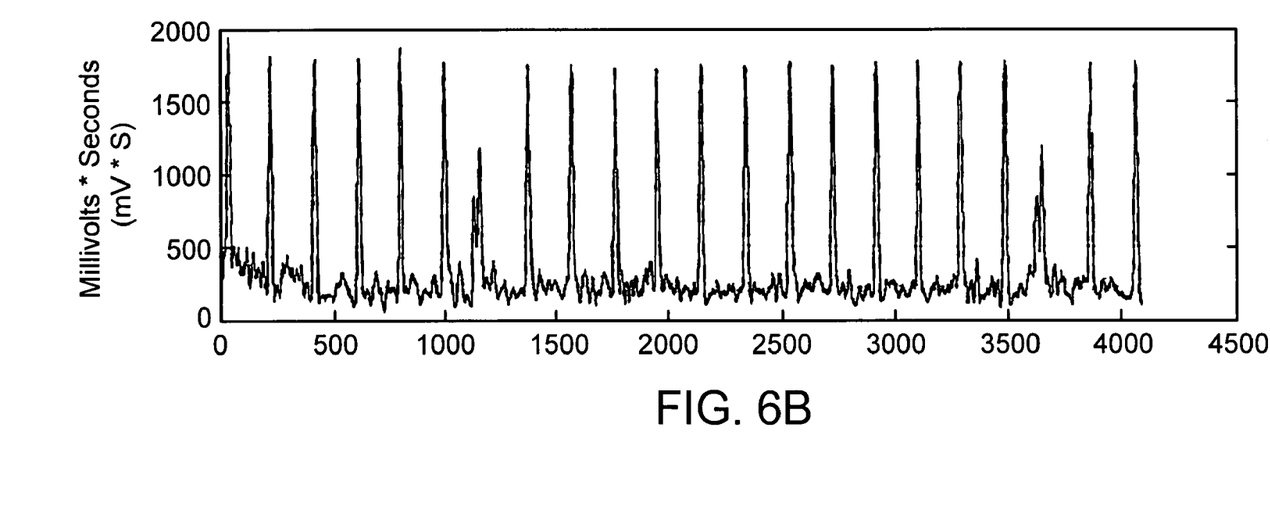
FIG. 6B illustrates the effect of the windowed line integral on the ECG signal shown in FIG. 6A.

FIG. 6A illustrates an electrical signal with three ECG series with two PVCs, one PVC at 1200 samples and the other PVC at 3700 samples. FIG. 6B illustrates the effect of the windowed line integral on the ECG signal shown in FIG. 6A. The linear transform eliminates the spikes that can trigger QRS detections in threshold based methods. The PVC detector 318 (FIG. 3) uses the line integrated signal value at the point of the original QRS detections. If the value of the line integrated signal is less than 75% of the average value of the line integrated signal at the detection points, a ventricular contraction is detected. To confirm the presence of a ventricular contraction, the width of the signal at 30% of the average signal value can be evaluated. A wide peak at this point is further evidence of a PVC.

Returning to FIG. 4, at step 404, the PVC detector 318 (FIG. 3) uses the peak values of the line integrated signal near the points of QRS detection from the original signal shown in FIG. 6A to calculate the average value of the line integrated peaks. The computed average values are stored in memory.

At step 406, the PVC detector 318 (FIG. 3) marks a line integrated peak value having a value that is less than about 75% of the average peak value as a premature ventricular contraction. In one embodiment, further analysis of the signal is performed to confirm that the peak is a premature ventricular contraction by checking if the width of the peak is about 30% of the average peak value. The thresholds were derived from empirical results by inspecting the data, selecting a threshold, performing further testing using the selected threshold and adjusting the threshold values based on the results of the tests. A threshold value from 70-80% and from 25%-45% can be selected dependent on the amount of muscle noise and amount of baseline wander in the signal. A wider peak is further evidence that a ventricular contraction has occurred. By detecting the ventricular activity in a line integrated space, the PVCs are detected in a way that does not require any assumptions about the morphology of the signal or the placement of the electrodes. This method is robust to false QRS detections on artifacts of the PVC that are not truly the ventricular contraction.

At step 408, after the premature ventricular contractions are detected, the true peak of the ventricular activity is identified by searching for the first local maximum following the peak detected in the line integrated signal. This local maximum is identified as the true QRS peak for the beat. For each PVC, the original QRS detection is replaced with the corrected detection in the R-R interval time series.

Figure 7:
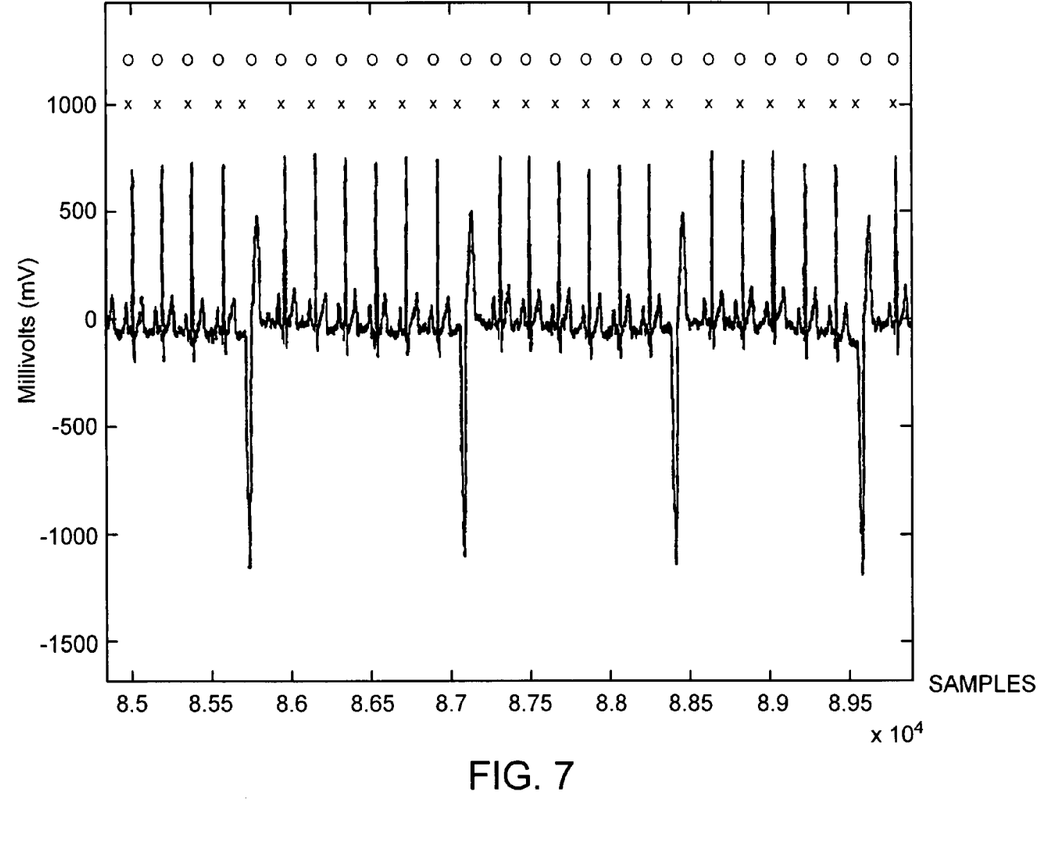
FIG. 7 shows the original ECG signal displayed on a user interface with labels "x" indicating each original QRS peak detection and labels 'o' indicating each corresponding corrected QRS peak detection.

FIG. 7 shows the original ECG signal displayed on a user interface with labels "x" indicating each original QRS peak detection and labels 'o' indicating each corresponding corrected QRS peak detection.

Figure 8A:
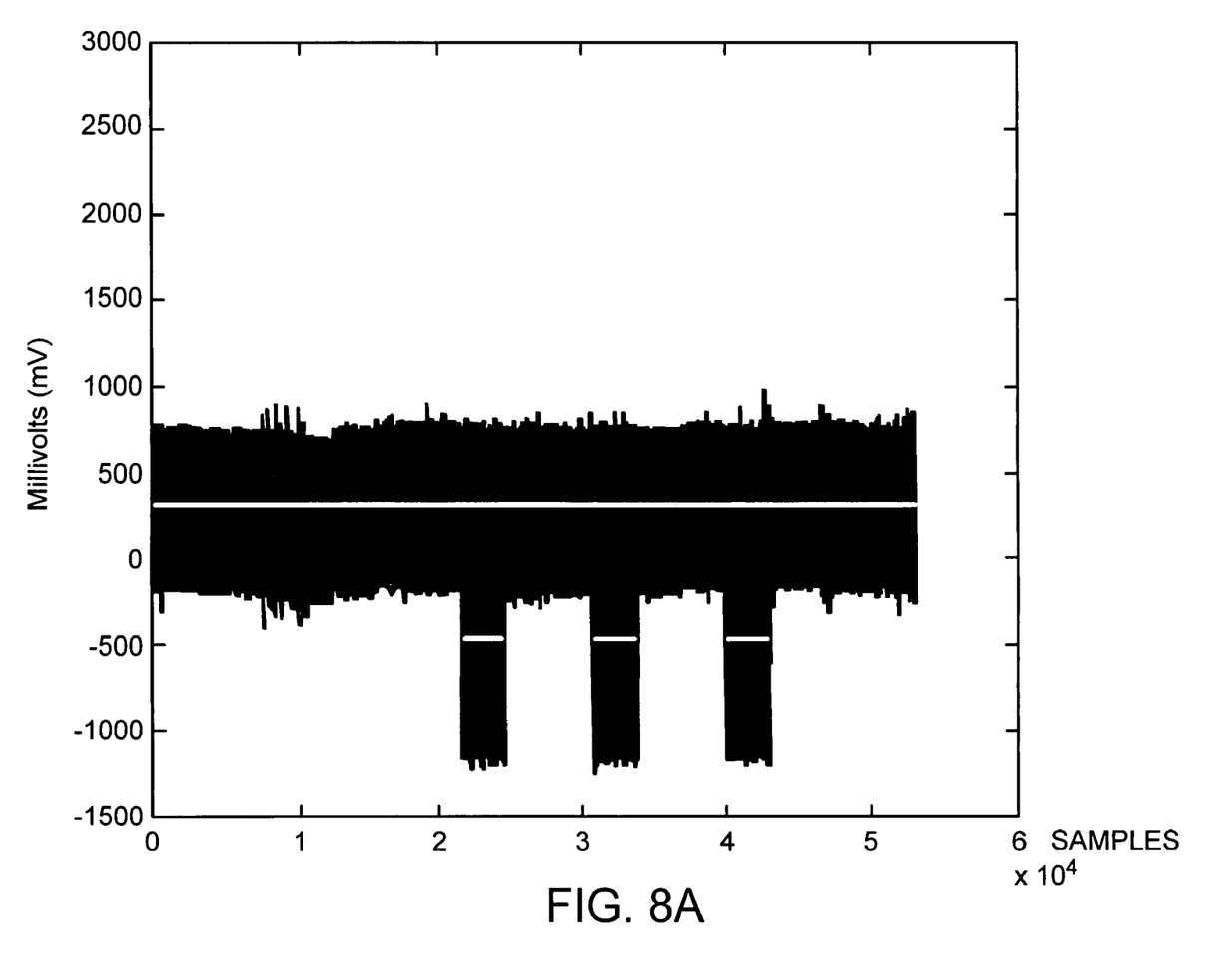
FIGS. 8A and 8B show the results of using the detector on four hours of simulated data.
Figure 8B:
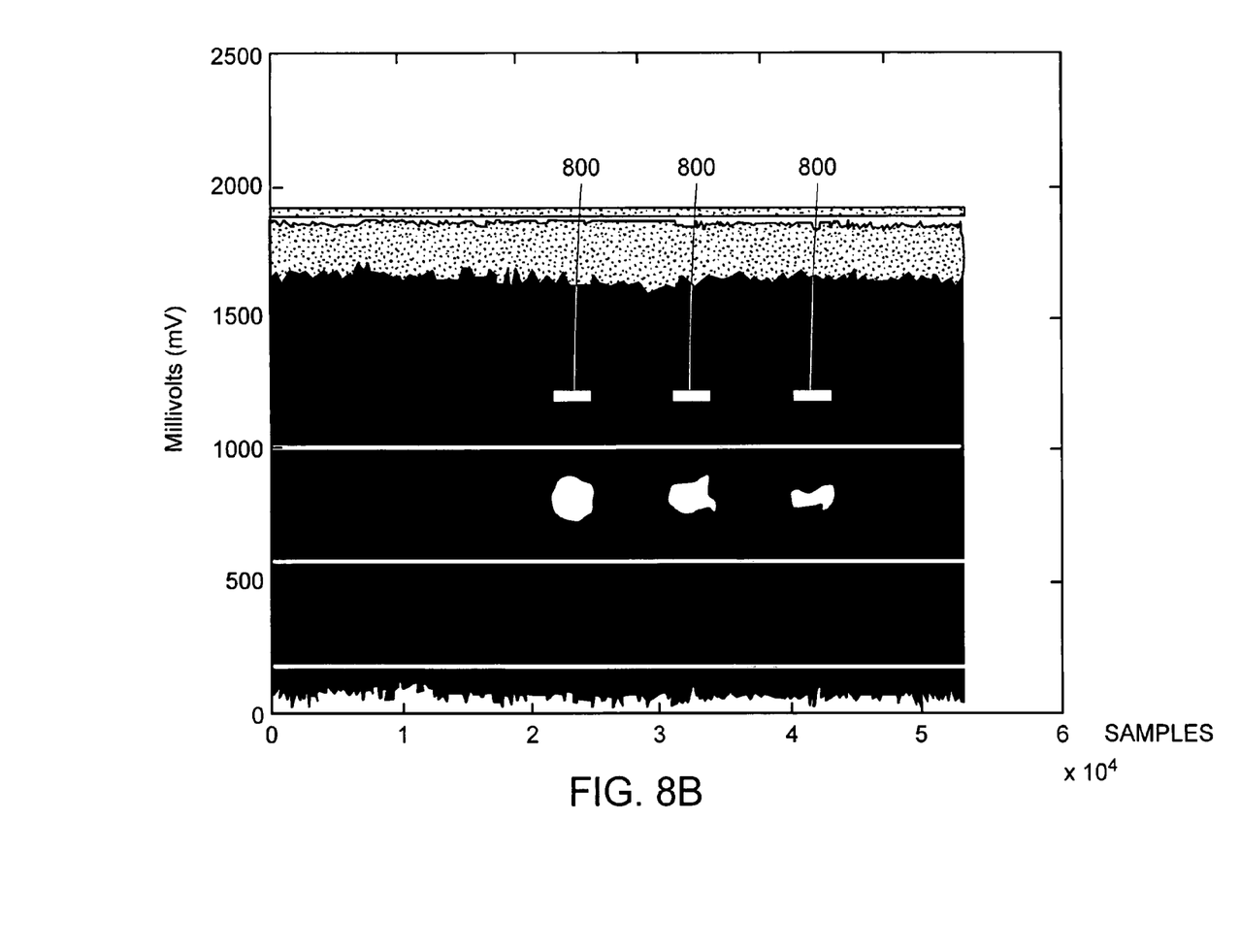

FIGS. 8A and 8B show the results of using the detector on four hours of simulated data. Running on over 15000 beats, the PVC detection system correctly identified and corrected all 480 PVCs in the record. The results shown in FIG. 8 were generated using a simulator. These results included a false detection that occurred on the first beat.

FIGS. 8A and 8B illustrate the results from the PVC detector 318 (FIG. 4). FIG. 8A illustrates three episodes of PVCs which can be distinguished by the larger downward spikes.

FIG. 8B illustrates the PVC regions detected by the algorithm in the line integrated space. The rectangular areas 800 indicate the detected PVCs.

It will be apparent to those of ordinary skill in the art that methods involved in the present invention may be embodied in a computer program product that includes a computer usable medium. For example, such a computer usable medium may consist of a read only memory device, such as a CD ROM disk or conventional ROM devices, or a random access memory, such as a hard drive device or a computer diskette, having a computer readable program code stored thereon. The invention has been described in an embodiment for correction of PVC in an EGT signal. The invention provides a higher quality output R-R interval time series because the position of the detected QRS complexes is corrected to the peak of the QRS complex instead of the onset of the QRS complex and thus, more accurate heart rate information is provided. The accurate heart rate information can be used in other tests for determining abnormal heart rates that are sensitive to R-R interval variablity and heart rate variability such as atrial fibrillation.

The PVC detector 318 (FIG. 3) is independent of any particular ECG morphology because it detects PVCs in a line integral transformed space. Thus, it can be used in non-standard lead placements and on an ECG signal generated by the ambulatory monitor that often contains significant muscle noise as the subject is ambulatory.

While this invention has been particularly shown and described with references to preferred embodiments thereof, it will be understood by those skilled in the art that various changes in form and details may be made therein without departing from the scope of the invention encompassed by the appended claims.

What is claimed is:

1. A computer implemented method for automatically detecting premature ventricular contraction in an ECG signal comprising:
    transforming the ECG signal to a line integrated signal having a plurality of peaks, each peak providing a peak value where the line integrated signal is at a maximum for the peak;
    computing an average of the peak values; and
    comparing each peak value with a threshold of the average of the peak values to provide an indication of whether the peak providing each peak value represents a premature ventricular contraction.

2. The method of claim 1, wherein comparing includes comparing each peak value with a threshold that is between seventy and eighty percent of the average of the peak values.

3. The method of claim 1, further comprising:
    comparing a width of a peak with an average width of the peaks to provide an indication of whether the peak indicates a premature ventricular contraction.

4. The method of claim 1, further comprising:
    correcting position of detected QRS complexes in the ECG signal corresponding to detected premature ventricular contractions based on comparing each peak value with the threshold of the average of the peak values.

5. A computer apparatus for automatically detecting a premature ventricular contraction in an ECG signal comprising:
    a PVC detector configured such that it transforms the ECG signal to a line integrated signal including a plurality of peaks, with each peak providing a peak value where the line integrated signal is at a maximum for the peak, computes an average of the peak values, and compares each peak value with a threshold of the average of the peak values to provide an indication of whether the peak corresponding to each peak value represents a premature ventricular contraction.

6. The apparatus of claim 5, wherein the PVC detector compares each peak value with a threshold that is between seventy and eighty percent of the average of the peak values.

7. The apparatus of claim 5, wherein the PVC detector also is configured to compare a width of a peak with an average width of the peaks to provide an indication of whether the peak indicates a premature ventricular contraction.

8. The apparatus of claim 5, further comprising:
    a PVC corrector which corrects a position of a detected QRS complex corresponding to a detected premature ventricular contraction based on comparing each peak value with a threshold of the average of the peak values.

9. An apparatus for automatically detecting a premature ventricular contraction in an ECG signal comprising:
    means for transforming the ECG signal to a line integrated signal having a plurality of peaks, each peak providing a peak value where the line integrated signal is at a maximum for the peak;
    means for computing an average of the peak values; and
    means for comparing each peak value with a threshold of the average of the peak values to provide an indication of whether the peak providing each peak value represents a premature ventricular contraction.

10. A computer program product for automatically detecting a premature ventricular contraction in an ECG signal, the computer program product comprising a computer usable medium having computer readable program code thereon, including program code which:
    transforms the ECG signal to a line integrated signal having a plurality of peaks with each peak providing a peak value where the line integrated signal is at a maximum for the peak;
    computes an average of the peak values; and
    compares each peak value with a threshold of the average of the peak values to provide an indication of whether the peak providing each peak value represents a premature ventricular contraction.

11. A computer implemented method for automatically detecting atrial fibrillation in an ECG signal comprising:
    detecting QRS complexes in the ECG signal;
    transforming the ECG signal to a line integrated signal having a plurality of peaks with each peak providing a peak value where the line integrated signal is at a maximum for the peak;
    computing an average of the peak values;
    comparing each peak value with a threshold of the average of the peak values to provide an indication of whether the peak providing each peak value represents a premature ventricular contraction; and
    correcting QRS detection in the ECG signal based on comparing each peak value with the threshold of the average of the peak values.

* * * * *